(12) United States Patent
Kim et al.

(10) Patent No.: US 6,531,446 B1
(45) Date of Patent: Mar. 11, 2003

(54) PEPTIDES HAVING BIOLOGICAL ACTIVITY

(75) Inventors: Sun-Chang Kim, Daejon (KR); Chan-Bae Park, Kyungki-Do (KR); Jae-Hyun Lee, Woolsan (KR); Seung-Suh Hong, Daejon (KR); Hyun-Soo Lee, Seoul (KR)

(73) Assignee: Korea Advanced Institute of Science and Technology, Taejon (KR)

( * ) Notice: Subject to any disclaimer, the term of this patent is extended or adjusted under 35 U.S.C. 154(b) by 0 days.

(21) Appl. No.: 09/600,710

(22) PCT Filed: Jan. 22, 1999

(86) PCT No.: PCT/KR99/00036

§ 371 (c)(1),
(2), (4) Date: Nov. 2, 2000

(87) PCT Pub. No.: WO99/37664

PCT Pub. Date: Jul. 29, 1999

(30) Foreign Application Priority Data

Jan. 22, 1998 (KR) .............................. 98-1797

(51) Int. Cl.[7] ............................ C07K 4/00; C07K 7/08; C07K 14/00; C12P 21/02
(52) U.S. Cl. ................ 514/2; 514/12; 514/13; 514/14; 514/15; 514/16; 514/17; 514/18; 530/300; 530/326; 530/327; 530/328; 530/329; 530/330; 530/344
(58) Field of Search .............. 514/2, 12, 13, 514/14, 15, 16, 17, 18; 530/300, 326, 327, 328, 329, 330, 344

(56) References Cited

U.S. PATENT DOCUMENTS 5,177,189 A * 1/1993 Dyer et al. ............. 530/324
5,856,435 A * 1/1999 Bazile et al. ............ 530/300
5,981,221 A * 11/1999 Hillman et al. ........... 435/69.1

FOREIGN PATENT DOCUMENTS

WO WO-9519370 A1 * 7/1995 ........... C07K/14/00
WO WO-9521931 A1 * 8/1995 ........... C12N/15/87

OTHER PUBLICATIONS

Kim et al., cDNA Cloning and Characterization of Buforinl, and Antimicrobial Peptide: A Cleavage Product of Histone H2A. Biochem. Biophys. Res. Commun. 229, 381–387 (1996).*

Biochemical and Biophysical Research Communications 218, 408–413 (1996).

FEBB Letters 389 (1966) 87–90.

Biochemical and Biophysical Research Communications 229, 381–387 (1996).

* cited by examiner

*Primary Examiner*—Christopher S. F. Low
*Assistant Examiner*—Chih-Min Kam
(74) *Attorney, Agent, or Firm*—Darby & Darby (57) ABSTRACT

The present invention relates to peptides that are more potent than or equally potent as the conventional antimicrobial peptides and has strong antimicrobial activities at high salt concentration.

16 Claims, 2 Drawing Sheets

SEQUENCE LISTING

```
<160> NUMBER OF SEQ ID NOS: 22

<210> SEQ ID NO 1
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 1

Arg Ala Gly Leu Gln Phe Pro Val Gly Arg Val His Arg Leu Leu Arg
1               5                   10                  15

Lys

<210> SEQ ID NO 2
<211> LENGTH: 16
<212> TYPE: PRT
<213> ORGANISM: Artificial Sequence
<220> FEATURE:
<223> OTHER INFORMATION: SYNTHETIC PEPTIDE

<400> SEQUENCE: 2

Ala Gly Leu Gln Phe Pro Val Gly Arg Val His Arg Leu Leu Arg Lys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: SYNTHETIC PEPTIDE

<400> SEQUENCE: 3

Gly Leu Gln Phe Pro Val Gly Arg Val His Arg Leu Leu Arg Lys
1               5                   10                  15

<210> SEQ ID NO 4
<211> LENGTH: 14
<212> TYPE: PRT
<213> ORGANISM: Artificial Sequence
<220> FEATURE:
<223> OTHER INFORMATION: SYNTHETIC PEPTIDE

<400> SEQUENCE: 4

Leu Gln Phe Pro Val Gly Arg Val His Arg Leu Leu Arg Lys
1               5                   10

<210> SEQ ID NO 5
```

```
<211> LENGTH: 13
<212> TYPE: PRT
<213> ORGANISM: Artificial Sequence
<220> FEATURE:
<223> OTHER INFORMATION: SYNTHETIC PEPTIDE

<400> SEQUENCE: 5

Gln Phe Pro Val Gly Arg Val His Arg Leu Leu Arg Lys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: SYNTHETIC PEPTIDE

<400> SEQUENCE: 6

Phe Pro Val Gly Arg Val His Arg Leu Leu Arg Lys
1               5                   10

<210> SEQ ID NO 7
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 7

Pro Val Gly Arg Val His Arg Leu Leu Arg Lys
1               5                   10

<210> SEQ ID NO 8
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 8

Thr Arg Ser Ser Arg Ala Gly Leu Gln Phe Pro Val Gly Arg Val His
1               5                   10                  15

Arg

<210> SEQ ID NO 9
<211> LENGTH: 16
<212> TYPE: PRT
<213> ORGANISM: Artificial Sequence
<220> FEATURE:
<223> OTHER INFORMATION: SYNTHETIC PEPTIDE

<400> SEQUENCE: 9

Arg Ala Gly Leu Gln Phe Pro Val Gly Arg Val His Arg Leu Leu Arg
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: SYNTHETIC PEPTIDE

<400> SEQUENCE: 10

Arg Ala Gly Leu Gln Phe Pro Val Gly Arg Val His Arg Leu Leu
1               5                   10                  15
```

```
<210> SEQ ID NO 11
<211> LENGTH: 14
<212> TYPE: PRT
<213> ORGANISM: Artificial Sequence
<220> FEATURE:
<223> OTHER INFORMATION: SYNTHETIC PEPTIDE

<400> SEQUENCE: 11

Arg Ala Gly Leu Gln Phe Pro Val Gly Arg Val His Arg Leu
1               5                  10

<210> SEQ ID NO 12
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 12

Arg Lys Gly Leu Gln Lys Leu Val Gly Arg Val His Arg Leu Leu Arg
1               5                  10                  15

Lys

<210> SEQ ID NO 13
<211> LENGTH: 20
<212> TYPE: PRT
<213> ORGANISM: Artificial Sequence
<220> FEATURE:
<223> OTHER INFORMATION: SYNTHETIC PEPTIDE

<400> SEQUENCE: 13

Arg Leu Leu Arg Arg Leu Leu Arg Arg Leu Leu Arg Arg Leu Leu Arg
1               5                  10                  15

Arg Leu Leu Arg
            20

<210> SEQ ID NO 14
<211> LENGTH: 21
<212> TYPE: PRT
<213> ORGANISM: Artificial Sequence
<220> FEATURE:
<223> OTHER INFORMATION: SYNTHETIC PEPTIDE

<400> SEQUENCE: 14

Arg Val His Arg Leu Leu Arg Arg Val His Arg Leu Leu Arg Arg Val
1               5                  10                  15

His Arg Leu Leu Arg
            20

<210> SEQ ID NO 15
<211> LENGTH: 21
<212> TYPE: PRT
<213> ORGANISM: Artificial Sequence
<220> FEATURE:
<223> OTHER INFORMATION: SYNTHETIC PEPTIDE

<400> SEQUENCE: 15

Arg Ala Gly Leu Gln Phe Pro Val Gly Arg Leu Leu Arg Arg Leu Leu
1               5                  10                  15

Arg Arg Leu Leu Arg
            20

<210> SEQ ID NO 16
<211> LENGTH: 17
<212> TYPE: PRT
```

```
<213> ORGANISM: Artificial Sequence
<220> FEATURE:
<223> OTHER INFORMATION: SYNTHETIC PEPTIDE WITH AMIDATION

<400> SEQUENCE: 16

Arg Ala Gly Leu Gln Phe Pro Val Gly Arg Val His Arg Leu Leu Arg
1               5                   10                  15

Lys

<210> SEQ ID NO 17
<211> LENGTH: 13
<212> TYPE: PRT
<213> ORGANISM: Artificial Sequence
<220> FEATURE:
<223> OTHER INFORMATION: SYNTHETIC PEPTIDE

<400> SEQUENCE: 17

Arg Ala Gly Leu Gln Phe Pro Val Gly Arg Leu Leu Arg
1               5                   10

<210> SEQ ID NO 18
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 18

Arg Ala Gly Leu Gln Phe Pro Val Gly Arg Leu Leu Arg Leu Leu
1               5                   10                  15

Arg

<210> SEQ ID NO 19
<211> LENGTH: 12
<212> TYPE: PRT
<213> ORGANISM: Artificial Sequence
<220> FEATURE:
<223> OTHER INFORMATION: SYNTHETIC PEPTIDE

<400> SEQUENCE: 19

Arg Leu Leu Arg Arg Leu Leu Arg Arg Leu Leu Arg
1               5                   10

<210> SEQ ID NO 20
<211> LENGTH: 16
<212> TYPE: PRT
<213> ORGANISM: Artificial Sequence
<220> FEATURE:
<223> OTHER INFORMATION: SYNTHETIC PEPTIDE

<400> SEQUENCE: 20

Arg Leu Leu Arg Arg Leu Leu Arg Arg Leu Leu Arg Arg Leu Leu Arg
1               5                   10                  15

<210> SEQ ID NO 21
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 21

Arg Leu Leu Arg
1
```

-continued

```
<210> SEQ ID NO 22
<211> LENGTH: 9
<212> TYPE: PRT
<213> ORGANISM: Artificial Sequence
<220> FEATURE:
<223> OTHER INFORMATION: SYNTHETIC PEPTIDE

<400> SEQUENCE: 22

Arg Ala Gly Leu Gln Phe Pro Val Gly
1               5
```

PEPTIDES HAVING BIOLOGICAL ACTIVITY

This application is 371 of PCT/KR99/00036 filed Jan. 22, 1999, which claims the benefits of foreign priority from Republic of Korea Application No. 1998/1797 filed Jan. 22, 1998.

TECHNICAL FIELD

The peptides of the present invention have stronger antimicrobial activities than conventional peptides and have the activity at high salt concentrations.

BACKGROUND ART

The present invention relates to biologically active peptides. Every animal on earth possesses biophylaxis systems to defend or protect itself from the infection by virus or bacteria. One of such systems is a non-specific immunity using antimicrobial peptides.

Antimicrobial peptides are considered as a new type of drug due to the following outstanding properties. Firstly, antimicrobial peptides show stronger antimicrobial activities than conventional antibiotics against a broad spectrum of microorganisms. Secondly, antimicrobial peptides have a high industrial applicability which is beneficial to the human body since the antimicrobial peptides show antimicrobial activity against foreign pathogens without destroying the host cells. Thirdly, there is a smaller chance to develop microbial resistance since the antimicrobial peptides show their activity by a mechanism that is totally different from that of the conventional antibiotics, which have serious problems of developing resistance. Studies on antimicrobial peptides began by isolating cecropin from an insect which has an under-developed immune system. After the first finding, magainin, bombinin from amphibians, defensins from mammals were isolated. The studies on antimicrobial peptides are actively performed, and to date, about 2,000 antimicrobial peptides have been identified and reported from species ranging from microorganisms to human.

However, there are several barriers to develop the above mentioned antimicrobial peptides as drugs. Firstly, the conventional antimicrobial peptides act at relatively high concentrations. For instance, in case of magainin, an antimicrobial peptide isolated from epidermis of an amphibian, the active concentration is 50–200 $\mu$g/ml (Zasloff M. (1987) Proc. Natl. Acad. Sci. USA, 84: 5449–5453) even though it is effective against Gram-positive and Gram-negative bacteria and fungi. This concentration range is quite high considering that the conventional antibiotics act against a specific microorganism in the range 0.1–1 $\mu$g/ml. Secondly, the antimicrobial activity of the antimicrobial peptides is sensitive to salt concentration. In case of cystic fibrosis that invades the human lung, for instance, the antimicrobial peptide was not effective due to an abnormal increase of the salt concentrations at the site of invasion (Goldman, M. J. et al. (1997) Cell, 88: 553–560).

Antimicrobial peptides isolated from Korean toad were reported by the present inventors in Biochemical and Biophysical Research Communications 218, 408–413 (1996). These antimicrobial peptides known as buforin I and buforin II showed strong antimicrobial activities against a broad-spectrum of microorganisms including Gram-positive and Gram-negative bacteria and fungi. Buforin I and buforin II also have antimicrobial activities at a concentration of 1–4 $\mu$g/ml, which is stronger than that of conventional antimicrobial peptides.

These antimicrobial peptides, however, are also sensitive to salt concentrations. Therefore, it has been desired to develop antimicrobial peptides that have an enhanced antimicrobial activities and are not sensitive to salt concentrations to have antimicrobial activities in vivo.

DISCLOSURE OF THE INVENTION

It is an object of the present invention to provide novel biologically active peptides.

Another object of the present invention is to provide peptides that have antimicrobial activities against a wide variety of microorganisms with stronger antimicrobial activities.

It is another object of the present invention to provide peptides that are insensitive to salt concentrations in potentiating the antimicrobial activity.

A further object of the present invention is to provide a secondary structure of peptides that are not sensitive to salt concentration in potentiating the antimicrobial activity.

Another object of the present invention is to provide a precursor peptide that could prepare biologically active peptides.

Still another object of the present invention is to provide cDNA that can code for biologically active peptides.

DETAILED DESCRIPTION OF THE INVENTION

The peptide of the present invention comprises a peptide having an amphiphilic α-helix structure.

Also the peptide of the present invention comprises a peptide that has an altered secondary structure of buforin II (Biochemical and Biophysical Research Communications 218, 408–413 (1996)).

The present inventors have shown that the secondary structure of buforin II comprises a random coil (1–4 residue), extended helix (5–10 residue) and normal α-helix (11–21 residue) structures, starting from the N-terminus.

In the structure of buforin II, the peptide sequence having normal α-helix structure (11–21 residue), i.e., Pro Val Gly Arg Val His Arg Leu Leu Arg Lys (SEQ ID NO: 7) has a strong antimicrobial activity. The present inventors have identified that a peptide, especially a peptide with at least the sequence forming the random coil structure (1–4 residue) is removed, has a very strong antimicrobial activity. Therefore, the group of peptides according to the present invention consists of peptides that contain an α-helix structure of buforin II, especially those having the Pro Val Gly Arg Val His Arg Leu Leu Arg Lys (SEQ ID NO: 7) sequence. These α-helix forming sequences, for instance the sequence Pro Val Gly Arg Val His Arg Leu Leu Arg Lys (SEQ ID NO: 7), can additionally have amino acids at the C- or N-terminus preferably amino acids forming extended helix or normal helix at the N-terminus or an amidated peptide at the C-terminus.

Another group of peptides according to the present invention comprises a peptide having a repeat unit of [Arg Leu Leu Arg]n (SEQ ID NO: 21) (n is an integer between 1 and 6), (Arg Leu Leu Arg (SEQ ID NO. 21) being the specific repeat pattern found in the amino acid sequence of buforin II) and preferably peptides where n=2–5.

The peptides can include additional amino acids at the C- or N-terminus, and the amino acid sequence at the N-terminus can include those that do not form a random coil, preferably those forming an extended helix. The group of amino acid sequence, for instance, includes Arg Ala Gly Leu Gln Phe Pro Val Gly[Arg Leu Leu Arg]$_1$ (SEQ ID NO: 1 7), Arg Ala Gly Leu Gln Phe Pro Val Gly[Arg Leu Leu Arg]$_2$ (SEQ ID NO: 18), Arg Ala Gly Leu Gln Phe Pro Val Gly[Arg Leu Leu Arg]$_3$ (SEQ ID NO: 15), [Arg Leu Leu Arg]$_3$ (SEQ ID NO: 19), [Arg Leu Leu Arg]$_4$ (SEQ ID NO: 20), [Arg Leu Leu Arg]$_5$ (SEQ ID NO: 13) and etc.

The peptides according to the present invention can be synthesized by well-known techniques in the field, for instance, by using an automatic peptide synthesizer or by using a genetic engineering technique. For instance, the peptide can be produced by constructing fusion gene composed of fusion partner and the peptide genes, transforming it into host microorganism, expressing the fusion protein in the host, cleaving the fusion protein with proteolytic enzyme or chemical agent, and purifying the antimicrobial peptide. For this purpose, for instance, a DNA sequence can be inserted between fusion partner and peptide genes to introduce a sequence encoding processing site which can be cleaved by proteases such as factor Xa and enterokinase, or by chemical agents such as CNBr and hydroxylamine.

To introduce DNA sequence encoding CNBr cleavage site, for instance, fusion partner and antimicrobial peptide genes can be in-frame fused by ligating the fusion partner gene digested at its 3-end with a restriction enzyme whose recognition sequence contains Met codon (ATG) in their recognition sequence, such as AflIII, BsmI, BspHI, BspLU11I, NcoI, NdeI, NsiI, Ppu10I, SphI, StyI, or their isoschizomers, and the peptide gene digested at its 5-end with a restriction enzyme whose cleavage site is compatible with the cleavage site of fusion partner. For another example, to introduce DNA sequence encoding hydroxylamine cleavage site, a DNA sequence encoding Asn-Gly can be introduced between fusion partner and peptide genes. For instance, fusion partner and peptide genes can be in-frame fused by ligating fusion partner gene digested at its 3-end with a restriction enzyme or its isoschizomer whose recognition sequence contains Asn codon in its recognition sequence, and the peptide gene digested at its 5-end with a restriction enzyme whose cleavage sequence containing Gly codon can be in-frame fused to the 3-end of fusion partner by compatible cohesive or blunt end.

The gene structure in the present invention can be introduced into host cell by cloning it into an expression vector such as plasmid, virus, or other conventional vehicle in which the gene can be inserted or incorporated.

The peptides according to the present invention contain C-terminal amidated forms.

The peptides according to the present invention show strong antimicrobial activities against a wide variety of microorganisms including Gram-negative and Gram-positive bacteria, fungi and protozoa.

The peptides according to the present invention can be administered with other biologically active pharmaceutical preparations such as biologically active chemicals, other peptide, and etc.

The amino acids in the present invention are abbreviated according to the IUPAC_IUB nomenclature as below.

| amino acid | abbreviation |
| --- | --- |
| Alanine | A |
| Arginine | R |
| Asparagine | N |
| Aspartic acid | E |
| Cysteine | C |
| Glutamic acid | D |
| Glutamine | Q |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophane | W |
| Tyrosine | Y |
| Valine | V |

The invention will be further illustrated by the following examples. It will be apparent to those having conventional knowledge in the field that these examples are given only to explain the present invention more clearly, but the invention is not limited to the examples given.

EXAMPLE 1

Preparation of Peptides

According to the sequence given in Table 1, a variety of peptides were synthesized by using an automatic peptide synthesizer and were purified by using a C18 reverse phase high performance liquid chromatography (Waters Associates, USA).

TABLE 1

Amino acid sequense of buforin II and its derivatives

| Peptide | Amino acid sequence |
| --- | --- |
| SEQ ID NO. 1 | Arg Ala Gly Leu Gln Phe Pro Val Gly Arg Val His Arg Leu Leu Arg Lys |
| SEQ ID NO. 2 | Ala Gly Leu Gln Phe Pro Val Gly Arg Val His Arg Leu Leu Arg Lys |
| SEQ ID NO. 3 | Gly Leu Gln Phe Pro Val Gly Arg Val His Arg Leu Leu Arg Lys |
| SEQ ID NO. 4 | Leu Gln Phe Pro Val Gly Arg Val His Arg Leu Leu Arg Lys |
| SEQ ID NO. 5 | Gln Phe Pro Val Gly Arg Val His Arg Leu Leu Arg Lys |
| SEQ ID NO. 6 | Phe Pro Val Gly Arg Val His Arg Leu Leu Arg Lys |
| SEQ ID NO. 7 | Pro Val Gly Arg Val His Arg Leu Leu Arg Lys |
| SEQ ID NO. 8 | Thr Arg Ser Ser Arg Ala Gly Leu Gln Phe Pro Val Gly Arg Val His Arg |
| SEQ ID NO. 9 | Arg Ala Gly Leu Gln Phe Pro Val Gly Arg Val His Arg Leu Leu Arg |
| SEQ ID NO. 10 | Arg Ala Gly Leu Gln Phe Pro Val Gly Arg Val His Arg Leu Leu |
| SEQ ID NO. 11 | Arg Ala Gly Leu Gln Phe Pro Val Gly Arg Val His Arg Leu |
| SEQ ID NO. 12 | Arg Lys Gly Leu Gln Lys Leu Val Gly Arg Val His Arg Leu Leu Arg Lys |
| SEQ ID NO. 13 | Arg Leu Leu Arg Arg Leu Leu Arg Arg Leu Leu Arg Arg Leu Leu Arg Arg Leu Leu Arg |

TABLE 1-continued

Amino acid sequense of buforin II and its derivatives

| Peptide | Amino acid sequence |
|---|---|
| SEQ ID NO. 14 | Arg Val His Arg Leu Leu Arg Arg Val His Arg Leu Leu Arg Arg Val His Arg Leu Leu Arg |
| SEQ ID NO. 15 | Arg Ala Gly Leu Gln Phe Pro Val Gly Arg Leu Leu Arg Arg Leu Leu Arg Arg Leu Leu Arg |
| SEQ ID NO. 16 | Arg Ala Gly Leu Gln Phe Pro Val Gly Arg Val His Arg Leu Leu Arg Lys-NH$_2$ |
| SEQ ID NO. 17 | Arg Ala Gly Leu Gln Phe Pro Val Gly Arg Leu Leu Arg |
| SEQ ID NO. 18 | Arg Ala Gly Leu Gln Phe Pro Val Gly Arg Leu Arg Arg Leu Leu Arg |
| SEQ ID NO. 19 | Arg Leu Leu Arg Arg Leu Leu Arg Arg Leu Leu Arg |
| SEQ ID NO. 20 | Arg Leu Leu Arg Arg Leu Leu Arg Arg Leu Leu Arg Arg Leu Leu Arg |

EXAMPLE 2

Estimation of Antimicrobial Activity

By using the peptides as in Example 1, the minimal inhibitory concentration of the peptides were determined against a variety of microorganisms. Bacteria and fungi were incubated overnight in Mller-Hinton and Saboraud media, respectively, at 37 and 30° C., respectively, and were inoculated in media for 2 hours to a midlogarithmic phase. After diluting the bacteria and fungi to $10^4$–$10^5$ per 1 ml, they were inoculated into a 96-well plate containing serially diluted peptides and incubated for additional 18 hours. The minimal inhibitory concentration was determined at a concentration that inhibits the growth of the microorganisms by measuring the absorbance. The results are shown in Table 2.

TABLE 2

Antimicrobial Activity of the peptides

Minimal Inhibitory Concentrations (μg/ml)

| Microorganisms | Buforin II | Seq No. 1 | Seq No. 2 | Seq No. 3 | Seq No. 4 | Seq No. 5 | Seq No. 6 | Seq No. 7 | Seq No. 8 | Seq No. 9 | Seq No. 10 | Seq No. 11 |
|---|---|---|---|---|---|---|---|---|---|---|---|---|
| Gram-positive | | | | | | | | | | | | |
| Bacillus subtilis | 2 | 1 | 4 | 4 | 8 | 18 | 32 | 25 | >200 | 12 | 50 | 100 |
| Staphylococcus aureus | 4 | 2 | 8 | 8 | 18 | 62 | 32 | 50 | >200 | 50 | 200 | 200 |
| Streptococcus mutans | 2 | 1 | 4 | 4 | 8 | 36 | 32 | 25 | >200 | 25 | 50 | 100 |
| Streptococcus pneumoniae | 4 | 2 | 4 | 4 | 18 | 18 | 32 | 50 | >200 | 25 | 100 | 100 |
| Gram-negative | | | | | | | | | | | | |
| Escherichia coli | 4 | 2 | 2 | 2 | 8 | 36 | 32 | 25 | >200 | 12 | 50 | 200 |
| Serratia sp. | 1 | 2 | 2 | 2 | 4 | 18 | 16 | 25 | >200 | 12 | 25 | 100 |
| Psudomonas putida | 4 | 2 | 2 | 2 | 8 | 36 | 32 | 50 | >200 | 25 | 50 | 200 |
| Salmonella typhimurium | 2 | 1 | 4 | 4 | 18 | 18 | 64 | 50 | >200 | 25 | 50 | 200 |
| Fungi | | | | | | | | | | | | |
| Candida albicans | 1 | 1 | 8 | 8 | 36 | 62 | 32 | 50 | >200 | 50 | >200 | >200 |
| Cryptococcus neoformans | 1 | 1 | 8 | 8 | 62 | 62 | >100 | 50 | >200 | 50 | 100 | 200 |
| Saccharomyces cerevisiae | 1 | 1 | 8 | 8 | 36 | 62 | >100 | 50 | >200 | 100 | >200 | >200 |

Minimal Inhibitory Concentrations (μg/m)

| Microorganisms | Buforin II | Seq No. 12 | Seq No. 13 | Seq No. 14 | Seq No. 15 | Seq No. 16 | Margainin 2 | Buf(5–13) [RLLR] | Buf(5–13) [RLLR]$_2$ | (RLLR)$_3$ | (RLLR)$_4$ |
|---|---|---|---|---|---|---|---|---|---|---|---|
| Gram-positive | | | | | | | | | | | |
| Bacillus subtilis | 2 | 18 | 2 | 6 | 1 | 1 | 50 | 32 | 4 | 16 | 2 |
| Staphylococcus aureus | 4 | 18 | 1 | 50 | 1 | 1 | 50 | 64 | 8 | 16 | 1 |
| Streptococcus mutans | 2 | 36 | 2 | 25 | 0.5 | 0.5 | 100 | 16 | 16 | 16 | 2 |
| Streptococcus pneumoniae | 4 | 18 | 2 | 100 | 1 | 1 | 50 | 32 | 8 | 16 | 2 |
| Gram-negative | | | | | | | | | | | |
| Escherichia coli | 4 | 18 | 2 | 100 | 1 | 2 | 100 | 32 | 8 | 32 | 2 |
| Serratia sp. | 1 | 4 | 1 | 3 | 1 | 1 | 25 | 32 | 8 | 16 | 1 |
| Psudomonas putida | 4 | 36 | 2 | 50 | 1 | 2 | 50 | 32 | 16 | 16 | 2 |
| Salmonella typhimurium | 2 | 18 | 2 | 50 | 1 | 2 | 50 | 16 | 4 | 16 | 2 |
| Fungi | | | | | | | | | | | |
| Candida albicans | 1 | 16 | 8 | >200 | 2 | 2 | 25 | 32 | 4 | 32 | 8 |
| Cryptococcus neoformans | 1 | 8 | 8 | 100 | 1 | 1 | 12 | 32 | 4 | 32 | 8 |
| Saccharomyces cerevisiae | 1 | 4 | 8 | >200 | 4 | 2 | 25 | 32 | 8 | 32 | 8 |

The peptide, Arg Ala Gly Leu Gln Phe Pro Val Gly(Arg Leu Leu Arg)$_3$ (SEQ ID NO: 15), that has a fused amino acid sequence forming extended <alpha>-helix at the N-terminus of (Arg Leu Leu Arg)$_3$ (SEQ ID NO: 19) showed an especially potent antimicrobial activity, and the peptide (Arg Leu Leu Arg)$_4$ (SEQ ID NO: 20) and (Arg Leu Leu Arg)$_5$ (SEQ ID NO: 13), which has 4 and 5 repetitions of Arg Leu Leu Arg, respectively, also showed strong antimicrobial activities.

The peptide that had a deletion of the sequence forming a random coil structure from buforin II also showed a potent antimicrobial activity, and the peptide that had an amidation at the N-terminus showed a more potent antimicrobial activity.

EXAMPLE 3

Estimation of Antimicrobial Activity as a Function of Salt Concentrations

Figure 1:
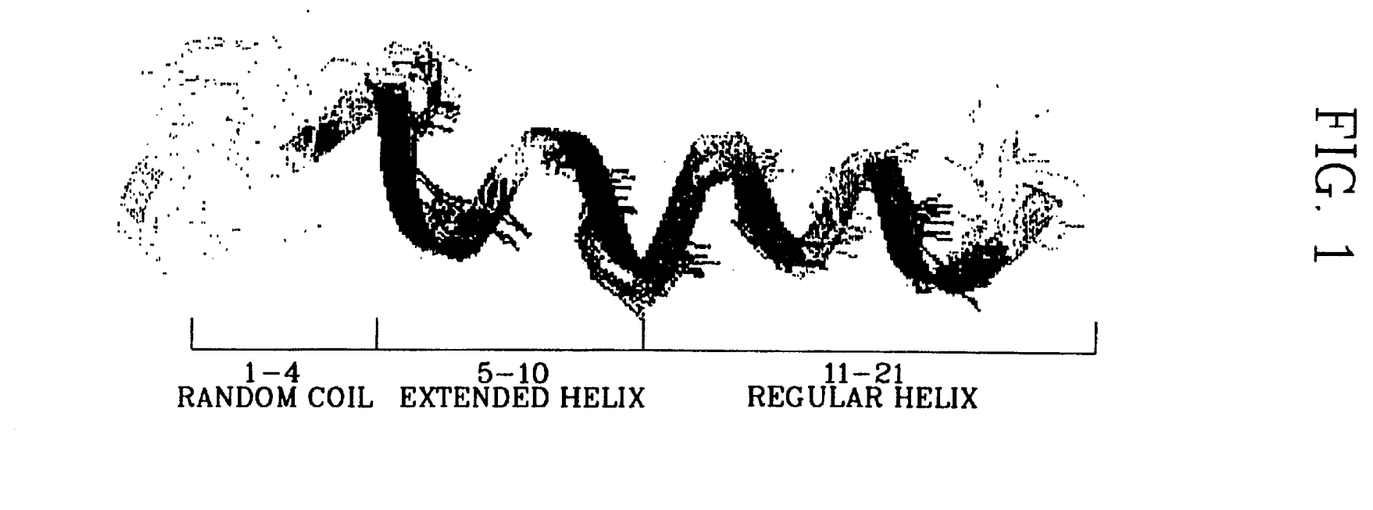
FIG. 1 is a secondary structure of buforin II determined by NMR spectrometry in the presence of 50% trifluoroethanol as a structure-forming agent.
Figure 2:
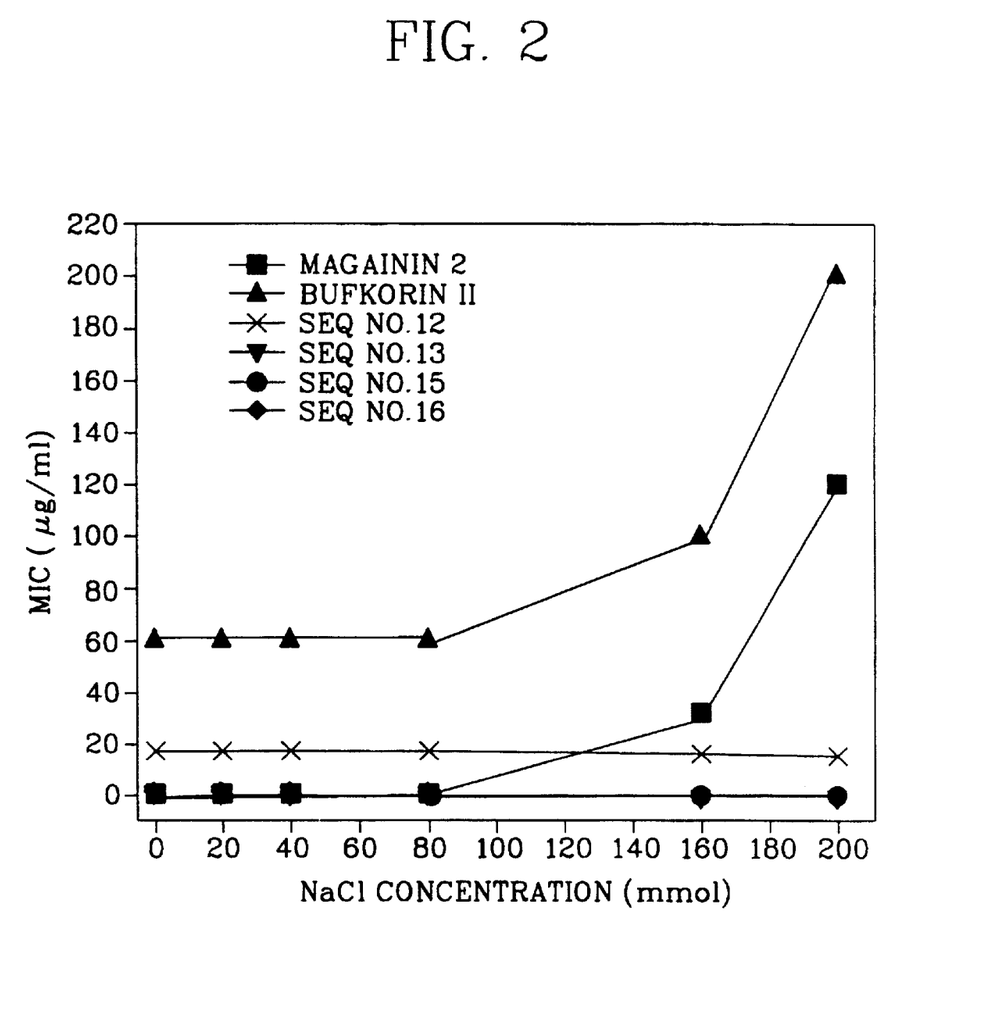
FIG. 2 is a graph showing the minimal inhibitory concentration as a function of a salt concentration.

The minimal inhibitory concentration of the peptides was measured as a function of salt concentrations to determine whether the antimicrobial activity is dependent on the salt concentrations. The method of estimating the minimal inhibitory concentration was identical as in Example 2 except that the concentration of NaCl was changed. The result is shown in FIG. 2. The antimicrobial activity of the peptides according to the present invention did not vary as a function of salt concentration whereas that of buforin and magainin changed sensitively as a function of salt concentrations.

What is claimed is:

1. A purified peptide consisting of (Arg Leu Leu Arg)$_m$ (SEQ ID NO: 21)$_m$ or Arg Ala Gly Leu Gln Phe Pro Val Gly (Arg Leu Leu Arg)$_n$ ((SEQ ID NO: 22)-(SEQ ID NO: 21)$_n$), wherein m is an integer between 2 and 6 and n is an integer between 1 and 6.

2. A purified peptide comprising sequence (Arg Leu Leu Arg)$_n$ (SEQ ID NO: 21)$_n$, wherein n is an integer between 2 and 6, and a Gly residue is fused to the N-terminus of the peptide.

3. A purified peptide comprising the sequence (Arg Leu Leu Arg)$_n$ (SEQ ID NO: 21)$_n$, wherein n is an integer between 2 and 6, and the C-terminus of the peptide is amidated.

4. A purified peptide comprising the sequence Arg Lys Gly Leu Gln Lys Leu Val Gly Arg Val His Arg Leu Leu Arg Lys (SEQ ID NO: 12), wherein the peptide forms an α-helix, and provided that buforin I and buforin II are excluded.

5. A purified peptide comprising the sequence Pro Val Gly Arg Val His Arg Leu Leu Arg Lys (SEQ ID NO: 7) or Arg Lys Gly Leu Gin Lys Leu Val Gly Arg Val His Arg Leu Leu Arg Lys (SEQ ID NO: 12), wherein the peptide forms an α-helix and the C-terminus of the peptide is amidated, and provided that buforin I and buforin II are excluded.

6. A peptide according to claim 1, wherein the peptide consists of an amino acid sequence selected from the group consisting of Arg Leu Leu Arg Arg Leu Leu Arg Arg Leu Leu Arg Arg Leu Leu Arg Arg Leu Leu Arg (SEQ ID NO: 13) and Arg Ala Gly Leu Gln Phe Pro Val Gly Arg Leu Leu Arg Arg Leu Leu Arg (SEQ ID NO: 15).

7. A purified peptide comprising an amino acid sequence selected from the group consisting of Arg Leu Leu Arg Arg Leu Leu Arg Arg Leu Leu Arg Arg Leu Leu Arg Arg Leu Leu Arg (SEQ ID NO: 13) and Arg Ala Gly Leu Gin Phe Pro Val Gly Arg Leu Leu Arg Arg Leu Leu Arg Arg Leu Leu Arg (SEQ ID NO: 15), wherein a Gly residue is fused to the N-terminus of said peptide.

8. A purified peptide comprising the amino acid sequence Arg Ala Gly Leu Gin Phe Pro Val Gly Arg Val His Arg Leu Leu Arg Lys-amide (SEQ ID NO: 16).

9. A purified peptide comprising an amino acid sequence selected from the group consisting of Arg Ala Gly Leu Gin Phe Pro Val Gly Arg Val His Arg Leu Leu Arg Lys (SEQ ID NO: 1) and Arg Ala Gly Leu Gln Phe Pro Val Gly Arg Val His Arg Leu Leu Arg Lys-amide (SEQ ID NO: 16), wherein a Gly residue is fused to the N-terminus of said peptide.

10. A method for inhibiting the growth of bacteria or fungi, comprising contacting the bacteria or fungi with an effective amount of a purified peptide consisting of the sequence (Arg Leu Leu Arg)$_n$ (SEQ ID NO: 21)$_n$, wherein n is an integer between 1 and 6, and the time and conditions of administration result in the inhibition of the growth of the bactera or fungi.

11. A method for inhibiting the growth of bacteria or fungi, comprising contacting the bacteria or fungi with an effective amount of a purified peptide consisting of sequence (Arg Leu Leu Arg)$_n$ (SEQ ID NO: 21)$_n$, wherein n is an integer between 1 and 6, a Gly residue is fused to the N-terminus of the purified peptide, and the time and conditions of administration result in the inhibition of the growth of the bacteria or fungi.

12. A method for inhibiting the growth of bacteria or fungi, comprising contacting the bacteria or fungi with an effective amount of a purified peptide consisting of sequence (Arg Leu Leu Arg)$_n$ (SEQ ID NO: 21)$_n$, wherein n is an integer between 1 and 6, the C-terminus of the purified peptide is amidated, and the time and conditions of administration result in the inhibition of the growth of the bacteria or fungi.

13. A purified peptide comprising sequence Arg Ala Gly Leu Gln Phe Pro Val Gly (Arg Leu Leu Arg)$_n$ ((SEQ ID NO: 22)-(SEQ ID NO: 21)$_n$), wherein n is an integer between 2 and 6, and a Gly residue is fused to the N-terminus of the peptide.

14. A purified peptide comprising sequence Arg Ala Gly Leu Gln Phe Pro Val Gly (Arg Leu Leu Arg)$_n$ ((SEQ ID NO: 22)-(SEQ ID NO: 21)$_n$), wherein n is an integer between 2 and 6, and the C-terminus of the peptide is amidated.

15. A purified peptide comprising the sequence Pro Val Gly Arg Val His Arg Leu Leu Arg Lys (SEQ ID NO:7) or Arg Lys Gly Leu Gln Lys Leu Val Gly Arg Val His Arg Leu Leu Arg Lys (SEQ ID NO: 12), wherein the peptide forms a helix and a Gly residue is fused to the N-terminus of the peptide, and provided that buforin I and buforin II are excluded.

16. A purified peptide consisting of the sequence Arg Ala Gly Leu Gln Phe Pro Val Gly Arg Val His Arg Leu Leu Arg Lys (SEQ ID NO:1) or Pro Val Gly Arg Val His Arg Leu Leu Arg Lys (SEQ ID NO:7).

* * * * *

UNITED STATES PATENT AND TRADEMARK OFFICE
CERTIFICATE OF CORRECTION

PATENT NO.   : 6,531,446 B1
DATED        : March 11, 2003
INVENTOR(S)  : Sun-Chang Kim It is certified that error appears in the above-identified patent and that said Letters Patent is hereby corrected as shown below:

<u>Title page,</u>
Item [73], Assignee, please add:
-- Samyang Genex Corporation, Seoul (KR) --

Signed and Sealed this

Twenty-sixth Day of August, 2003

JAMES E. ROGAN
*Director of the United States Patent and Trademark Office*